(12) United States Patent
Denny et al.

(10) Patent No.: US 8,515,685 B2
(45) Date of Patent: Aug. 20, 2013

(54) METHOD OF MASS SPECTROMETRY, A MASS SPECTROMETER, AND PROBABILISTIC METHOD OF CLUSTERING DATA

(75) Inventors: Richard Denny, Newcastle-unde-Lyme (GB); Keith Richardson, High Peak (GB)

(73) Assignee: Micromass UK Limited, Manchester (GB)

( * ) Notice: Subject to any disclaimer, the term of this patent is extended or adjusted under 35 U.S.C. 154(b) by 1342 days.

(21) Appl. No.: 11/568,437

(22) PCT Filed: May 3, 2005

(86) PCT No.: PCT/GB2005/001674
§ 371 (c)(1),
(2), (4) Date: Aug. 20, 2007

(87) PCT Pub. No.: WO2005/106920
PCT Pub. Date: Nov. 10, 2005

(65) Prior Publication Data
US 2008/0318213 A1 Dec. 25, 2008

(30) Foreign Application Priority Data

Apr. 30, 2004 (GB) .................................. 0409676.4
May 20, 2004 (GB) .................................. 0411251.2

(51) Int. Cl.
*G01N 33/50* (2006.01)

(52) U.S. Cl.
USPC ................. 702/23; 702/19; 702/30; 702/179; 703/2; 703/11; 703/12; 707/737; 73/23.37; 73/659

(58) Field of Classification Search
None
See application file for complete search history.

(56) References Cited

U.S. PATENT DOCUMENTS

| | | | |
|---|---|---|---|
| 5,087,815 A | 2/1992 | Schultz et al. | |
| 5,545,894 A | 8/1996 | Funsten et al. | |
| 5,679,950 A | 10/1997 | Baba et al. | |
| 5,910,655 A | 6/1999 | Skilling | |
| 6,393,367 B1 | 5/2002 | Tang et al. | |
| 6,446,010 B1 | 9/2002 | Eriksson et al. | |
| 6,489,608 B1 | 12/2002 | Skilling | |
| 6,556,651 B1 | 4/2003 | Thomson et al. | |
| 8,012,764 B2 | 9/2011 | Denny et al. | |
| 2002/0192720 A1 | 12/2002 | Parker et al. | |
| 2003/0052264 A1 | 3/2003 | Baba et al. | |
| 2003/0077840 A1 | 4/2003 | Chait et al. | |
| 2003/0111596 A1 | 6/2003 | Becker et al. | |
| 2005/0065732 A1* | 3/2005 | Tilton et al. ..................... 702/19 |
| 2006/0003460 A1 | 1/2006 | Appel et al. | |
| 2006/0234326 A1 | 10/2006 | Cerda | |
| 2008/0138909 A1 | 6/2008 | Wheeler et al. | |
| 2008/0185516 A1 | 8/2008 | Baba et al. | |
| 2009/0057550 A1 | 3/2009 | Stults et al. | |

FOREIGN PATENT DOCUMENTS

| | | |
|---|---|---|
| EP | 1 043 676 A2 | 10/2000 |
| EP | 1 319 954 A1 | 6/2003 |
| EP | 1 598 666 A1 | 11/2005 |
| GB | 2 391 699 A | 2/2004 |
| GB | 2 394 545 A | 4/2004 |
| WO | WO 02/086168 A1 | 10/2002 |
| WO | WO 02/096540 A1 | 12/2002 |
| WO | WO 03/095978 A3 | 11/2003 |
| WO | WO 03/098182 A2 | 11/2003 |

OTHER PUBLICATIONS

Hopfgartner, et al., "Exact Mass Measurement of Product Ions for the Structural Elucidation of Drug Metabolites with a Tandem Quadrupole Orthogonal-Acceleration Time-of-Flight Mass Spectrometer", Journal of American Society for Mass Spectrometry, vol. 10, pp. 1305-1314, Jul. 5, 1999.
Borchers, et al., "Preliminary comparison of precursor scans and liquid chromatography-tandem mass spectrometry on a hybrid quadrupole time-of-flight mass spectrometer", Journal of Chromatography A, vol. 854, pp. 119-130, 1999.
Bylund, et al., "Chromatographic alignment by warping and dynamic programming as a pre-processing tool for PARAFAC modeling of liquid chromatography-mass spectrometry data", Journal of Chromatography A, 961, No. 2, May 8, 2002, pp. 237-244, XP004370624.
Charlwood, et al., "Structural Characterisation of N-Linked Glycan Mixtures by Precursor Ion Scanning and Tandem Mass Spectrometric Analysis", Rapid Communications in Mass Spectrometry, vol. 13, pp. 1522-1530, May 31, 1999.
De Hoffmann, "Tandem Mass Spectrometry: a Primer", Journal of Mass Spectrometry, Dec. 8, 1995, pp. 129-137, Vo. 31, XP007903162.
Gulcicek, et al., "Structural Elucidation in the Millisecond Time Frame Using Fast In-Source CID API Time-of-Flight MS", ASMS Conference 1998, Book of Abstracts, pp. 891.
Hellerstein, et al., "Mass isotopomer distribution analysis at eight years: theoretical, analytic and experimental considerations", American Physiology, vol. 276, No. 39, 1999, pp. E1146-E1170, XP002978087.
Preuss, et al., "Quantitative Analysis of Multicomponent Mass Spectra", AIP Conference Proceedings AIP USA, No. 617, 2002, pp. 155-162, XP007900817.
Huang, et al., "Characterization of Cyclodextrins Using Ion-evaporation Atmospheric-pressure Ionization Tandem Mass Spectrometry", Rapid Communications in Mass Spectrometry, vol. 4, No. 11, pp. 467-471, 1990.
Jain, et al., "Statistical Pattern Recognition: A Review", IEEE Transactions on Pattern Analysis and Machine Intelligence, IEEE Service Center, Los Alamitos, CA, US Vo. 22, No. 1, Jan. 20000, pp. 4-37, XP000936788, ISSN: 0162-8828.
Kang, et al., "Radical detection in a methane plasma", J. Vac. Sci. Technol. A, vol. 21, No. 6, Nov./Dec. 2003, pp. 1978-1980, XP007900816.

(Continued)

*Primary Examiner* — Eric S Dejong
(74) *Attorney, Agent, or Firm* — Muirhead and Saturnelli, LLC

(57) ABSTRACT

A mass spectrometer and a method of spectrometry are disclosed wherein liquid chromatography mass spectral data are probabilistically clustered on the basis of mass to charge ratio and retention time.

25 Claims, 4 Drawing Sheets

(56) References Cited

OTHER PUBLICATIONS

Figure 1A:
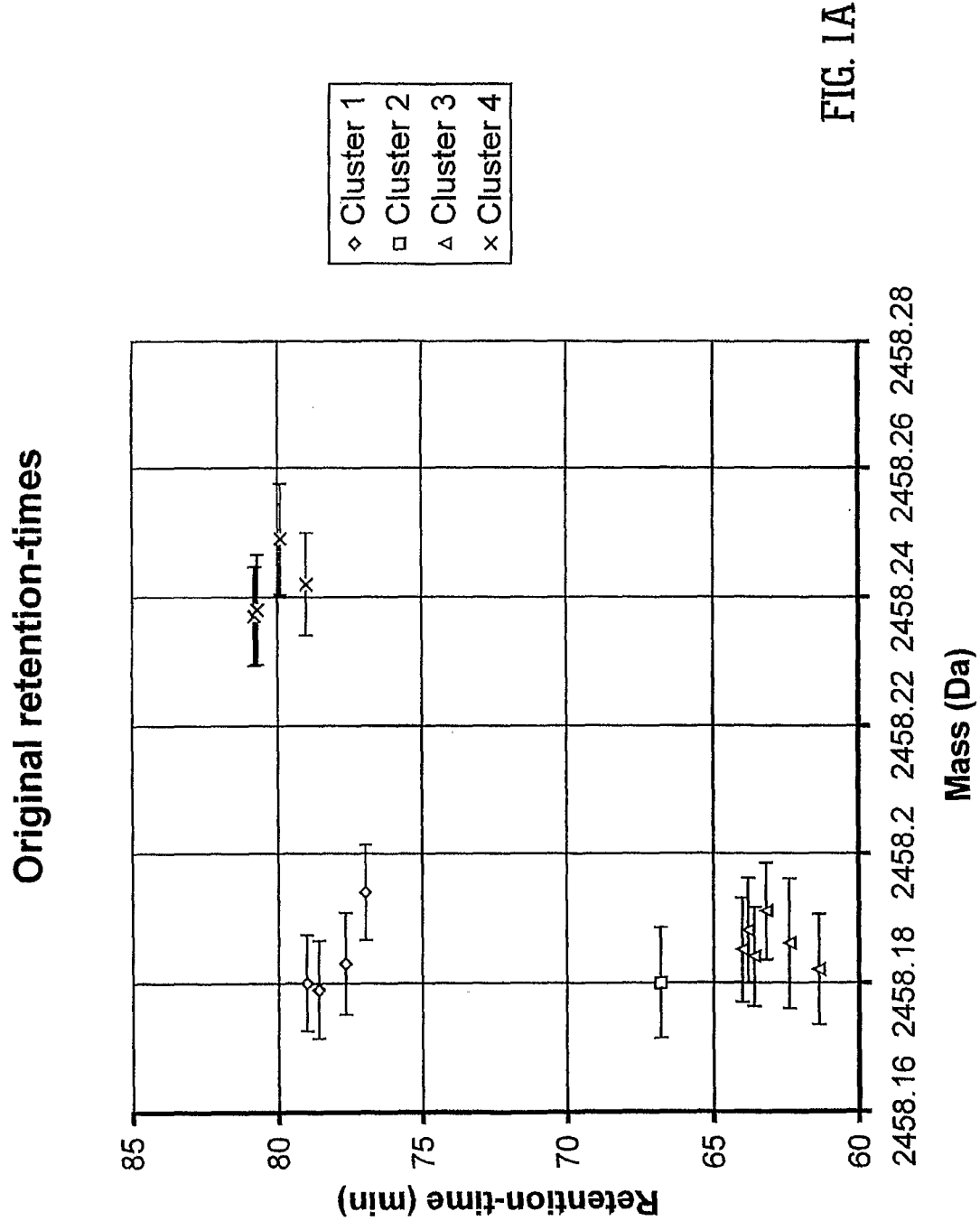

Morris, et al., "High Sensitivity Collisionally-activated Decomposition Tandem Mass Spectrometry on a Novel Quadrupole/Orthogonal-acceleration Time-of-flight Mass Spectrometer", Rapid Communications in Mass Spectrometry, vol. 10, pp. 879-896, 1996.

Morris, et al., "A Novel Geometry Mass Spectrometer, the Q-TOF, for Low-Femtomole/Attomole-Range Biopolymer Sequencing", Journal of Protein Chemistry, vol. 16, No. 5, pp. 469-479, 1997.

Yost, et al., "Tandem Quadrupole Mass Spectrometry", John Wiley & Sons, Ch. 8, pp. 175-195, 1983.

\* cited by examiner

METHOD OF MASS SPECTROMETRY, A MASS SPECTROMETER, AND PROBABILISTIC METHOD OF CLUSTERING DATA

CROSS REFERENCE TO RELATED APPLICATIONS

This application is the National Stage of International Application No. PCT/GB05/01674, filed on May 3, 2005, which claims priority to and benefit of United Kingdom Patent Application No. 0409676, filed Apr. 30, 2004, and United Kingdom Patent Application No. 0411251, filed May 20, 2004. The entire contents of these applications are incorporated herein by reference.

The present invention relates to a method of mass spectrometry and a mass spectrometer. The preferred embodiment relates to the clustering, associating or grouping of data relating to peptide digest products obtained by liquid chromatography mass spectrometry ("LC-MS"). The data is preferably clustered by virtue of mass or mass to charge ratio and chromatographic retention time. In particular, mass spectral data relating to separate acquisitions or experimental runs is preferably associated and analysed. Furthermore, changes or differences in the relative concentrations, intensities or expression levels of analytes such as peptides or proteins in two or more different samples may be detected or recognised. Analytes which are expressed differently in two different samples may then be subsequently identified.

A non-hierarchical clustering method known as k-means clustering is known. This clustering method could in theory be applied to the problem of how to associate or cluster data relating to liquid chromatography mass spectrometry experiments which has been acquired in separate acquisitions or experiments.

The known k-means clustering approach involves classifying n data points into k clusters. Each point or datum is assigned to a cluster whose average value on a set of d variables is nearest to its centroid by some distance measure (usually Euclidean) on that set. Such assignments can be computed iteratively until reassigning points and recomputing centroids (over all points in a cluster) produces no further changes.

However, k-means clustering suffers from the problem that the number of clusters k needs first to be specified before clustering can be performed. Also, k-means clustering only finds specific locations for the cluster centres rather than integrating over all the possible locations of the cluster centres. The ad hoc distance criterion also cannot properly be normalised to give a probability of association between two data points.

A person skilled in the art will therefore appreciate that there are various limitations inherent with using k-means clustering to cluster LC-MS data. The preferred embodiment relates to a completely different approach to clustering LC-MS data which involves a probabilistic or Bayesian approach to clustering LC-MS data.

By way of background, Bayesian probability theory handles probabilities of statements. Probabilities tell how certain those statements are true. For example, a probability of 1 means that there is absolute certainty. A probability of 0 also means that there is absolute certainty, but absolute certainty that the statement is false. A probability of 0.5 means that there is maximum uncertainty whether the statement is true or false.

Changing probabilities when getting new information is an important aspect of Bayesian reasoning. So called Bayes rule defines how a rational agent changes its beliefs when it gets new information (evidence).

Bayesian probabilities or certainties are always conditional. This means that probabilities are estimated in the context of some background assumptions. Conditional probabilities may be written using the notation P(Thing|Assumption). The probabilities are numbers between zero and one, that tell how certain it is that Thing is true when it is believed that the Assumption is true. Conditional probabilities are often written in the form P(D|M) or P(M|D), where M is dependency model and D is data. Accordingly, P(D|M) means the probability of obtaining data D if it is believed that model M is the true model. Likewise, P(M|D) means the probability that the model M is the true model given the data D. Sometimes probabilities are presented just as P(M) or P(D), but these are imprecise Bayesian notations, since all the probabilities are actually conditional. However, sometimes, when all the terms have the same background assumptions then it may not be necessary to repeat them. In theory, probabilities should be written in the form P(D|M,U) and P(M|D,U) and P(M|U) and P(D|U), where U is a set of background assumptions.

Expert systems often calculate the probabilities of interdependent events by giving each parent event a weighting. Bayesian Belief Networks are considered to provide a mathematically correct and therefore more accurate method of measuring the effects of events on each other. The mathematics involved enable calculations to be made in both directions. So it is possible, for example, to find out which event was the most likely cause of another.

The following Product Rule of probability for independent events is well known:

$$p(AB)=p(A)*p(B)$$

where p(AB) means the probability of A and B happening.

This is a special case of the following Product Rule for dependent events, where p(A|B) means the probability of A given that B has already occurred:

$$p(AB)=p(A)*p(B|A)$$

$$p(AB)=p(B)*p(A|B)$$

So because:

$$p(A)p(B|A)=p(B)p(A|B)$$

Then:

$$p(A|B)=(p(A)*p(B|A))/p(B)$$

The above equation is a simpler version of Bayes' Theorem. This equation gives the probability of A happening given that B has happened, calculated in terms of other probabilities which are known.

Bayes' theorem can be summarised as:

$$P(H_0 | E) = \frac{P(E | H_0)P(H_0)}{P(E)}$$

$H_0$ can be taken to be a hypothesis which may have been developed ab initio or induced from some preceding set of observations, but before the new observation or evidence E. The term $P(H_0)$ is called the prior probability of $H_0$. The term $P(E|H_0)$ is the conditional probability of seeing the observation E given that the hypothesis $H_0$ is true—as a function of $H_0$ given E, it is called the likelihood function. The term P(E) is called the marginal probability of E and it is a normalizing constant and can be calculated as the sum of all mutually exclusive hypotheses:

$$\Sigma P(E|H_i) P(H_i)$$

The term $P(H_0|E)$ is called the posterior probability of $H_0$ given E. The scaling factor $P(E|H_0)/P(E)$ gives a measure of the impact that the observation has on belief in the hypothesis. If it is unlikely that the observation will be made unless the particular hypothesis being considered is true, then this scaling factor will be large. Multiplying this scaling factor by the prior probability of the hypothesis being correct gives a measure of the posterior probability of the hypothesis being correct given the observation.

The keys to making the inference work is the assigning of the prior probabilities given to the hypothesis and possible alternatives, and the calculation of the conditional probabilities of the observation under different hypotheses.

In view of the fact that there are certain limitations in attempting to using a k-clustering approach to dealing with LC-MS data, it is desired to provide an improved method of correctly clustering, associating or grouping LC-MS data.

According to an aspect of the present invention there is provided a method of mass spectrometry comprising:

determining a first physico-chemical property and a second physico-chemical property of components, molecules or analytes in a first sample, wherein the first physico-chemical property comprises the mass or mass to charge ratio and the second physico-chemical property comprises the elution time, hydrophobicity, hydrophilicity, migration time, or chromatographic retention time;

determining a first physico-chemical property and a second physico-chemical property of components, molecules or analytes in a second sample, wherein the first physico-chemical property comprises the mass or mass to charge ratio and the second physico-chemical property comprises the elution time, hydrophobicity, hydrophilicity, migration time, or chromatographic retention time; and probabilistically associating, clustering or grouping data relating to components, molecules or analytes in the first sample with data relating to components, molecules or analytes in the second sample.

According to the preferred embodiment the method further comprises determining a first physico-chemical property and a second physico-chemical property of components, molecules or analytes in one or more further samples, wherein the first physico-chemical property comprises the mass or mass to charge ratio and the second physico-chemical property comprises the elution time, hydrophobicity, hydrophilicity, migration time, or chromatographic retention time.

A likely error of the first physico-chemical property and/or a likely error of the second physico-chemical property are preferably determined.

Components, molecules or analytes in the first sample and/or the second sample and/or further samples are preferably separated by liquid chromatography. According to an embodiment components, molecules or analytes in the first sample and/or the second sample and/or further samples are separated from other components, molecules or analytes: (i) High Performance Liquid Chromatography ("HPLC"); (ii) anion exchange; (iii) anion exchange chromatography; (iv) cation exchange; (v) cation exchange chromatography; (vi) ion pair reversed-phase chromatography; (vii) chromatography; (vii) single dimensional electrophoresis; (ix) multi-dimensional electrophoresis; (x) size exclusion; (xi) affinity; (xii) revere phase chromatography; (xiii) Capillary Electrophoresis Chromatography ("CEC"); (xiv) electrophoresis; (xv) ion mobility separation; (xvi) Field Asymmetric Ion Mobility Separation ("FAIMS"); or (xvi) capillary electrophoresis.

A single data set is preferably formed from data relating to the first sample and/or data relating to the second sample and/or data relating to further samples. A sample number is preferably assigned to data in the single data set.

The step of probabilistically associating, clustering or grouping data relating to components, molecules or analytes in the first sample with data relating components, molecules or analytes in the second sample preferably further comprises using or adopting a method of trial and error and determining the most probable association, clustering or grouping of data.

Preferably, data points related to components, molecules or analytes in the first sample are compared with data points related to components, molecules or analytes in the second sample and/or data points related to components, molecules or analytes in further samples.

Each data point preferably comprises a value of the first physico-chemical property and/or a value of the second physico-chemical property. The data points are preferably divided or separated into mass or mass to charge ratio bins having a width of x Daltons wherein x is preferably selected from the group consisting of: (i) 1.0000-1.0001; (ii) 1.0001-1.0002; (iii) 1.0002-1.0003; (iv) 1.0003-1.0004; (v) 1.0004-1.0005; (vi) 1.0005-1.0006; (vii) 1.0006-1.0007; (viii) 1.0007-1.0008; (ix) 1.0008-1.0009; (x) 1.0009-1.0010; (xi) <1.0000; (xii) >1.0010; and (xiii) 1.0005.

The data is preferably initially clustered, grouped or associated into one or more first clusters of data points. The step of clustering the data points into one or more first clusters of data points preferably comprises probabilistically clustering the data points although less preferably other approaches may be used to initially cluster the data.

The preferred method preferably further comprises assessing the closeness of data points on a pairwise basis. The step of assessing the closeness of data points on a pairwise basis preferably comprises assessing the closeness of data points in a mass or mass to charge ratio bin given determined mass errors or mass to charge ratio errors on a pairwise basis.

The preferred method further comprises calculating probabilistically the likelihood that two data points relate to the same component, molecule or analyte. Preferably, the method further comprises determining pairwise probabilities $p_{ij}$ that two data points relate to the same component, molecule or analyte.

According to the preferred embodiment the method further comprises arranging the pairwise probabilities $p_{ij}$ in a matrix. Preferably, one or more trial truth tables are assigned to the matrix. The method preferably further comprises checking whether or not the matrix is self consistent by determining whether or not the matrix obeys a transitivity property. The transitivity property preferably comprises $b_{jk}=b_{ij}$ AND $b_{ik}$. If the matrix does not obey the transitivity property then the method preferably further comprises rejecting the trial truth table. If the matrix does obey the transitivity property then the method preferably further comprises assigning a probability to the trial truth table.

According to an embodiment the method further comprises assigning further trial truth tables to the matrix. In a similar manner to before, the method preferably checks whether or not the matrix is self consistent by determining whether or not the matrix obeys a transitivity property which preferably comprises $b_{jk}=b_{ij}$ AND $b_{ik}$. If the matrix does not obey the transitivity property then the method further comprises rejecting the further trial truth table. If the matrix does obey the transitivity property then the method further comprises assigning a probability to the further trial truth tables.

A particularly preferred aspect of the preferred embodiment comprises determining the most probable truth table.

According to a less preferred embodiment the data may initially be clustered, grouped or associated into one or more first clusters of data points comprises using k-means clustering or other methods known per se.

Once the data has been initially clustered, preferably using a probabilistic approach but less preferably using other approaches, the clustering of data is then optionally tested to see whether it can be improved upon. It is possible that at the end of this optional testing the clustering of data may not have substantially changed. Indeed, according to an embodiment it is contemplated that the data may be optimally initially clustered by the disclosed probabilistic clustering method and the further steps do not result in any initial improvement in the clustering of data.

According to the preferred embodiment the method preferably further comprises probabilistically clustering the data points into one or more second clusters of data points. The method may comprise maximising the overall probability or equivalently of the one or more second clusters of data points. This may involve moving or putting data points into new clusters of data points. Preferably, each data point may be moved or put into the same cluster as a data point having the nearest higher or lower value of the first physico-chemical property and/or the second physico-chemical property. According to an embodiment each data point may be moved or put into its own cluster if it is initially in the same cluster as a neighbouring data point. Preferably, the method further comprises iteratively modifying the cluster to which a or each data point is initially considered to belong until substantially no further improvement is found. The method of iteratively modifying the cluster to which a or each data point is initially considered to belong may continue until a pre-assigned iteration limit is reached.

According to a particularly preferred aspect of the preferred embodiment the method further comprises interrogating the one or more second (or less preferably first) clusters of data points to determine one or more third clusters of data points which preferably include one and only one data point representing a molecule, analyte or ion from the first sample, the second sample and any further samples.

However, it is contemplated that according to less preferred embodiments this strict requirement may sometimes be dropped especially if there is a large amount of data. Accordingly, according to a less preferred embodiment the method may further comprise interrogating the one or more second (or less preferably first) clusters of data points to determine one or more third clusters of data points which generally (but not necessarily exclusively) include one data point representing a molecule, analyte or ion from the first sample, the second sample and any further samples.

Preferably, the data points relating to the third clusters of data points are assumed to have or assigned a high level of certainty or are assumed to have or are assigned a value of true or one. These data points then act as internal reference points.

Preferably, the data relating to the second physico-chemical property of molecules, analytes or ions in at least some or each of the one or more third clusters of data points is averaged to form an average value for the second physico-chemical property. Preferably, data of the one or more data points which is clustered to form the third clusters of data points is adjusted such that the average value becomes the value of the second physico-chemical property for the data points.

Once the internal reference points have been assigned an average value of the second physico-chemical property (e.g. retention time) then either the remaining data or more preferably the whole data set is then realigned or calibrated in relation to these internal references.

According to the preferred embodiment the method preferably further comprises determining a calibration function to correlate or correct data relating to the observed second physico-chemical property with the average value for the second physico-chemical property. The calibration function may comprise a cubic spline function, a polynomial function or a probabilistic calibration function.

Preferably, the method further comprises adjusting data points from each sample or from all samples to align recalibrate, correct or reassign the second physico-chemical property for all data sets. Once the data has been realigned or recalibrated then the method preferably further comprises determining or assigning an error for the second physico-chemical property (e.g. retention time).

The preferred method preferably further comprises comparing adjusted data points related to components, molecules or analytes in the first sample with adjusted data points related to components, molecules or analytes in the second sample and/or adjusted data points related to components, molecules or analytes in further samples.

Each adjusted data point preferably comprises an unadjusted value of the first physico-chemical property and/or an adjusted value of the second physico-chemical property.

The adjusted data points are preferably divided or separated into mass or mass to charge ratio bins having a width of x Daltons wherein x is preferably selected from the group consisting of: (i) 1.0000-1.0001; (ii) 1.0001-1.0002; (iii) 1.0002-1.0003; (iv) 1.0003-1.0004; (v) 1.0004-1.0005; (vi) 1.0005-1.0006; (vii) 1.0006-1.0007; (viii) 1.0007-1.0008; (ix) 1.0008-1.0009; (x) 1.0009-1.0010; (xi)<1.0000; (xii) >1.0010; and (xiii) 1.0005.

According to the preferred embodiment the method preferably further comprises clustering the adjusted data points into one or more fourth clusters of data points.

The step of clustering the adjusted data points into one or more fourth clusters of data points preferably comprises probabilistically clustering the data points in a similar manner to before. The method therefore preferably comprises assessing the closeness of adjusted data points on a pairwise basis, wherein the step of assessing the closeness of adjusted data points on a pairwise basis comprises assessing the closeness of adjusted data points in a mass or mass to charge ratio bin given determined mass errors or mass to charge ratio errors on a pairwise basis.

The method preferably further comprises calculating probabilistically the likelihood that two adjusted data points relate to the same component, molecule or analyte. The method preferably further comprises determining pairwise probabilities that two adjusted data points relate to the same component, molecule or analyte.

According to the preferred embodiment the pairwise probabilities $p_{ij}$ are preferably arranged in a second matrix. One or more second truth tables are preferably assigned to the second matrix. A check is preferably made as to whether or not the second matrix is self consistent by determining whether or not the second matrix obeys a transitivity property. The transitivity property preferably comprises $b_{jk}=b_{ij}$ AND $b_{ik}$.

If the second matrix does not obey the transitivity property then the method preferably further comprises rejecting the second trial truth table. If the second matrix does obey the transitivity property then the method preferably further comprises assigning a probability to the second trial truth table.

According to the preferred embodiment the method further comprises assigning further second trial truth tables to the second matrix. The method preferably further comprises checking whether or not the second matrix is self consistent by determining whether or not the second matrix obeys a transitivity property. Preferably, the transitivity property comprises $b_{jk}=b_{ij}$ AND $b_{ik}$. If the second matrix does not obey the transitivity property then the method preferably further comprises rejecting the further second trial truth table. If the second matrix does obey the transitivity property then the method preferably further comprises assigning a probability to the second further trial truth tables.

According to an embodiment the method further comprises determining the most probable second truth table.

According to a less preferred embodiment the step of clustering the data into one or more fourth clusters of data points comprises using k-means clustering.

The preferred embodiment preferably comprises probabilistically clustering the adjusted data points into one or more fifth clusters of data points. This step is optional but not essential.

The preferred embodiment preferably comprises maximising the overall probability or equivalently of the one or more fifth clusters of data points. This preferably involves moving or putting data points into new clusters of data points. Preferably, each data point is moved or put into the same cluster as a data point having the nearest higher or lower value of the first physico-chemical property and/or the second physico-chemical property. Preferably, each data point is moved or put into its own cluster if it is initially in the same cluster as a neighbouring data point. The method preferably further comprises iteratively modifying the cluster to which a or each data point is initially considered to belong until substantially no further improvement is found.

According to an embodiment the method further comprises iteratively modifying the cluster to which a or each data point is initially considered to belong until a pre-assigned iteration limit is reached.

According to an embodiment the method comprises determining the intensity of first components, molecules or analytes in the first sample and/or first components, molecules or analytes in the second sample and/or first components, molecules or analytes in further samples.

Preferably, the intensity of the first components, molecules or analytes in the first sample is compared with corresponding first components, molecules or analytes in the second sample and/or further samples, wherein the first components, molecules or analytes belong to the same association, clustering or grouping of data. The first sample and/or the second sample and/or further samples may comprise a plurality of different biopolymers, proteins, peptides, polypeptides, oligionucleotides, oligionucleosides, amino acids, carbohydrates, sugars, lipids, fatty acids, vitamins, hormones, portions or fragments of DNA, portions or fragments of CDNA, portions or fragments of RNA, portions or fragments of mRNA, portions or fragments of tRNA, polyclonal antibodies, monoclonal antibodies, ribonucleases, enzymes, metabolites, polysaccharides, phosphorolated peptides, phosphorolated proteins, glycopeptides, glycoproteins or steroids.

Preferably, the first sample and/or the second sample and/or further samples comprise at least 2, 5, 10, 20, 30, 40, 50, 60, 70, 80, 90, 100, 200, 300, 400, 500, 600, 700, 800, 900, 1000, 1500, 2000, 2500, 3000, 3500, 4000, 4500, or 5000 components, molecules or analytes having different identities.

The first sample and/or the second sample and/or further samples may comprise a non-equimolar heterogeneous complex mixture.

The components, molecules or analytes in the first sample are preferably substantially the same as the components, molecules or analytes in the second sample and/or further samples.

The components, molecules or analytes are preferably endogenous or exogenous to the first sample and/or the second sample and/or further samples.

According to an embodiment either: (i) the first sample is taken from a diseased organism and the second sample is taken from a non-diseased organism; (ii) the first sample is taken from a treated organism and the second sample is taken from a non-treated organism; or (iii) the first sample is taken from a mutant organism and the second sample is taken from a wild type organism.

Preferably, the method further comprises identifying one or more of the components, molecules or analytes in the first sample and/or the second sample and/or further samples.

According to an embodiment one or more components, molecules or analytes in the first sample and/or one or more components, molecules or analytes in the second sample and/or one or more components, molecules or analytes in further samples are only identified if the intensity of one or more components, molecules or analytes in the first sample differ from the intensity of one or more components, molecules or analytes in the second sample and/or further samples by more than a predetermined amount.

According to an embodiment one or more components, molecules or analytes in the first sample and/or one or more components, molecules or analytes in the second sample and/or one or more components, molecules or analytes in further samples are only identified if the average intensity of a plurality of different components, molecules or analytes in the first sample differs from the average intensity of a plurality of different components, molecules or analytes in the second sample and/or further samples by more than a predetermined amount.

The predetermined amount is preferably selected from the group consisting of: (i) 1%; (ii) 2%; (iii) 5%; (iv) 10%; (v) 20%; (vi) 50%; (vii) 100%; (viii) 150%; (ix) 200%; (x) 250%; (xi) 300%; (xii) 350%; (xiii) 400%; (xiv) 450%; (xv) 500%; (xvi) 1000%; (xvii) 5000%; and (xviii) 10000%.

According to an aspect of the present invention there is provided a mass spectrometer comprising:

means arranged to determine a first physico-chemical property and a second physico-chemical property of components, molecules or analytes in a first sample, wherein the first physico-chemical property comprises the mass or mass to charge ratio and the second physico-chemical property comprises the elution time, hydrophobicity, hydrophilicity, migration time, or chromatographic retention time;

means arranged to determine a first physico-chemical property and a second physico-chemical property of components, molecules or analytes in a second different sample, wherein the first physico-chemical property comprises the mass or mass to charge ratio and the second physico-chemical property comprises the elution time, hydrophobicity, hydrophilicity, migration time, or chromatographic retention time; and means arranged to probabilistically associate, cluster or group components, molecules or analytes in the first sample with components, molecules or analytes in the second sample.

The mass spectrometer preferably comprises a liquid chromatograph. According to an embodiment the mass spectrometer further comprises one or mass filters and/or one or more mass analysers. The one or more mass filters and the one or more mass analysers are selected from the group consisting of: (i) an orthogonal acceleration Time of Flight mass analyser; (ii) an axial acceleration Time of Flight mass analyser; (iii) a Paul 3D quadrupole ion trap mass analyser; (iv) a 2D or linear quadrupole ion trap mass analyser; (v) a Fourier Transform Ion Cyclotron Resonance mass analyser; (vi) a magnetic sector mass analyser; (vii) a quadrupole mass analyser; and (viii) a Penning trap mass analyser.

The mass spectrometer preferably further comprises an ion source. The ion source preferably comprises a pulsed ion source or a continuous ion source. The ion source is preferably selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; and (xvi) a Nickel-63 radioactive ion source.

According to an aspect of the present invention there is provided a method of mass spectrometry comprising:

determining a first physico-chemical property and a second physico-chemical property of components, molecules or analytes in a first sample;

determining a first physico-chemical property and a second physico-chemical property of components, molecules or analytes in a second sample; and probabilistically associating, clustering or grouping components, molecules or analytes in the first sample with components, molecules or analytes in the second sample.

Preferably, the first physico-chemical property comprises: (i) mass or mass to charge ratio; (ii) isotopic or decharged mass or mass to charge ratio; or (iii) mono-isotopic or deisotoped mass or mass to charge ratio.

Preferably, the second physico-chemical property comprises chromatographic retention time.

Preferably, the second physico-chemical property is selected from the group consisting of: (i) solubility; (ii) molecular volume or size; (iii) net charge, charge state, ionic charge or composite observed charge state; (iv) isoelectric point (pI); (v) dissociation constant (pKa); (vi) antibody affinity; (vii) electrophoretic mobility; (viii) ionisation potential; (ix) dipole moment; (x) hydrogen-bonding capability or hydrogen-bonding capacity; and (xi) ion mobility in gas phase.

According to an aspect of the present invention there is provided a mass spectrometer comprising:

means arranged to determine a first physico-chemical property of components, molecules or analytes in a first sample;

means arranged to determine a first physico-chemical property of components, molecules or analytes in a second different sample; and means arranged to probabilistically associate, cluster or group components, molecules or analytes in the first sample with components, molecules or analytes in the second sample.

According to an aspect of the present invention there is provided a probabilistic method of clustering liquid chromatography mass spectrometry peptide data from different acquisitions comprising:

measuring the retention times and masses of a plurality of ions from related samples in different experimental acquisitions;

generating a data set comprising the masses and retention times along with estimates of the uncertainties inherent in each measurement;

associating data between different acquisitions using mass and retention time;

calculating average retention times where the associations give rise to clusters having one and only one representative from each experimental acquisition;

using the average retention times as reference points to calibrate the retention times for each acquisition; and associating data using mass and retention time as strongly as is warranted by the precision of the chromatography and the quality of the calibration.

Preferably, the association of data is achieved by dividing the data into mass bins of 1.0005 Da.

Preferably, the method further comprises for each mass bin determining the pair-wise probability of association of each pair of data in that mass bin.

Preferably, the method further comprises determining a probability for any trial clustering of the data in the mass bin by combining the pair-wise probabilities.

According to the preferred embodiment the method further comprises finding a plausible initial clustering of the data in mass and retention time by thresholding the pair-wise probabilities.

Preferably, the method further comprises finding the most probable clustering by local search with the plausible initial clustering as a starting point.

The step of associating data between different acquisitions preferably using mass and retention times preferably comprises using retention time as a weaker constraint than mass.

According to an aspect of the present invention there is provided a method of mass spectrometry comprising:

probabilistically associating, clustering or grouping components, molecules or analytes in a first sample or data relating to components, molecules or analytes in a first sample with components, molecules or analytes in a second sample or data relating to components, molecules or analytes in a second sample.

According to an aspect of the present invention there is provided a mass spectrometer comprising:

means arranged to probabilistically associate, cluster or group components, molecules or analytes in a first sample or data relating to components, molecules or analytes in a first sample with components, molecules or analytes in a second sample or data relating to components, molecules or analytes in a second sample.

According to an aspect of the present invention there is provided a method of mass spectrometry comprising:

associating, clustering or grouping components, molecules or analytes in a first sample or data relating to components, molecules or analytes in a first sample with components, molecules or analytes in a second sample or data relating to components, molecules or analytes in a second sample.

According to an aspect of the present invention there is provided a mass spectrometer comprising:

means arranged to associate, cluster or group components, molecules or analytes in a first sample or data relating to components, molecules or analytes in a first sample with components, molecules or analytes in a second sample or data relating to components, molecules or analytes in a second sample.

According to an aspect of the present invention there is provided a method of mass spectrometry comprising associating, clustering or grouping data.

According to an aspect of the present invention there is provided a mass spectrometer comprising means arranged to associate, cluster or group data.

The preferred embodiment relates to clustering liquid chromatography mass spectrometry (LC-MS) data acquired in separate experimental acquisitions, preferably on the basis of mass or mass to charge ratio and retention time e.g. chromatographic retention time. Advantageously, the preferred approach does not require samples to use a separate calibrant which is added to the samples in order to locate or recognise the same species of analyte in different experimental data. The use of calibrants which are introduced to samples can interfere with or suppress data. A calibrant may however be used periodically for a different purpose in experimental runs namely to ensure that the settings of mass spectrometer do not drift.

The preferred embodiment relates to processing LC-MS data and clustering such data. However, less preferably the disclosed probabilistic or Bayesian approach to clustering data could also be applied to Gas Chromatography Mass Spectrometry (GC-MS) data and other types of analysis wherein components, molecules or analytes are separated in time from other components.

According to the preferred embodiment a probabilistic measure is used to assess the closeness of data points on a pair-wise basis. This measure compares the hypothesis that the data arose from a single cluster against the hypothesis that the data arose from two distinct clusters considered a priori to be distributed randomly with uniform probability preferably within the mass-retention time plane.

In one dimension, where the clusters may appear in an interval $\Delta$ with uniform probability, a mean (of a Poisson distribution) of $\langle N \rangle$ clusters being expected and the positions of two data points are $x_i$ and $x_j$, the probability that two data points are associated with the same cluster is given by:

$$Pr(x_i, x_j \text{ from same cluster}) = p_{ij} = \frac{L(x_i, x_j)}{L(x_i, x_j) + \frac{\langle N \rangle}{\Delta}}$$

where the mean $\langle N \rangle$ represents a flexible prior preference for the number of clusters as opposed to a predetermined number k as used in k-means clustering.

In the above equation, $L(x_i, x_j)$ is a probabilistic calculation of the likelihood that two data points $x_i$ and $x_j$ are data points relating to the same component, molecule or analyte (i.e. peptide digest product) present within two separate experimental acquisitions.

Assuming Gaussian errors and a uniform prior probability distribution for the location of clusters the likelihood that two data points relate to the same peptide can be given as:

$$L(x_i, x_j) = \frac{1}{\sqrt{2\pi(\sigma_i^2 + \sigma_j^2)}} e^{-\frac{1}{2}\frac{(x_i - x_j)^2}{(\sigma_i^2 + \sigma_j^2)}}$$

where $\sigma_i$ and $\sigma_j$ are the uncertainties in the positions $x_i$ and $x_j$ respectively. This generalizes to two or more dimensions.

The probability measure $p_{ij} \in [0,1]$ has the interpretation that two data belong to the same cluster rather than different clusters. Unlike k-means clustering, this probability has been integrated over all possible positions of the cluster centre.

Any trial configuration of clusters of the data can be assigned an overall probability Q by combining the pair-wise probability values $p_{ij}$ defined by the probability measure:

$$\log(Pr(\text{cluster configuration})) \propto Q = \sum_{i=1}^{M} \left[ \left( \sum_{j<i, j \in C_i} \log(p_{ij}) \right) + \left( \sum_{k<i, k \notin C_i} \log(1 - p_{ik}) \right) \right]$$

where $C_i$ is set of data assigned to the cluster to which datum is assigned and M is the number of data points.

Once an initial viable trial configuration of clusters is found, it is preferably incrementally improved upon by seeking to maximize the overall probability or equivalently Q of the cluster.

According to the preferred embodiment some of the analytes relating to peptide digest products are preferably initially clustered using a matrix method. According to this method, the pair-wise probabilities $p_{ij}$ of two data points relating to the same species of peptide digest product are initially arranged in a matrix. The matrix preferably comprises the pair-wise probabilities $p_{ij}$ that every two data points are associated with the same cluster. For example, the following matrix represents the probabilities that the data points in each of the combinations of pairs of four data points A-D are related to the same cluster:

|   | A | B | C | D |
|---|---|---|---|---|
| A | X | 0.8 | 0.3 | 0.1 |
| B |   | X | 0.15 | 0.2 |
| C |   |   | X | 0.7 |
| D |   |   |   | X |

In the above example, the matrix shows the probability $p_{ij}$ that point A is related to the same cluster as point B as being 0.8. Points A and B may therefore be considered reasonably likely to relate to the same cluster. In contrast, the probability $p_{ij}$ that point B relates to the same cluster as point D is 0.2. This may therefore be considered reasonably unlikely.

The matrix may then be analysed at various thresholds, between 0 and 1, so that those probabilities below the threshold are assigned a value of false (e.g. 0) whilst those above the threshold are assigned a value of true (e.g. 1) indicating which data are associated with the same cluster.

The resultant matrix of Boolean values $b_{ij}$ may not represent a viable cluster configuration as they may not obey the necessary transitivity property:

$$b_{jk} = b_{ij} \text{ AND } b_{ik}$$

The above condition is therefore preferably checked. If the transitivity property is not met then the trial truth table is preferably rejected.

The thresholding scheme may be generalized to act on various reconstructions of the matrix of pair-wise probabilities. These are preferably produced iteratively by decrementing the number of largest eigenvalues and corresponding eigenvectors of the original matrix to be used in the reconstructed matrix.

In the preferred embodiment, an initial cluster configuration may then be improved upon by considering orderings of the data points on the basis of mass and chromatographic retention time. The clusters to which data points belong can then be modified according to an iterative scheme for each ordering. According to this scheme, each datum may be put into a new cluster. It is also put into the previous datum's cluster, if distinct. It is also put into the next datum's cluster, if distinct.

This process may be repeated until no further improvement is found or a pre-assigned iteration limit is reached.

In the preferred embodiment the data is preferably divided into nominal mass ranges or bins. The difference in mass between the centres of two adjacent mass bins is preferably large enough such that data relating to different peptides do not fall into the same mass bin.

Amino acids have a mass sufficiency which varies from about 1.00009 to about 1.00074, with a mean mass sufficiency of approximately 1.00047. Accordingly, biological samples commonly exhibit a periodicity of approximately 1.0005 atomic mass units (Daltons) and hence the bins preferably are arranged to have a mass range of 1.0005 Da which corresponds to the mass of an average peptide baryon.

Multiple data for the same peptide tend to concentrate around the centre of a single mass bin. The likelihood of the data falling into an adjacent mass bin due to errors is therefore very low. As such, the data in different bins can be considered to relate to different peptides i.e. different clusters.

A particularly preferred aspect of the preferred embodiment is the alignment of the retention-time axes for the data from each acquisition. This is highly advantageous since reported retention times are usually uncalibrated and systematic differences often occur between data sets from each acquisition. The correct realignment of retention times from two data sets is therefore advantageous and the ability of the preferred embodiment to perform this step represents an important advance in the art.

In the preferred embodiment an initial pass of clustering is performed with only a relatively weak contribution from the proximity of data in retention time. This may be achieved by assigning large values to the retention time uncertainties for each datum.

Resulting clusters that have one and only one representative from each acquisition are used to form a list of potential reference points (with uncertainties) by taking averages (and standard deviations). Outliers are preferably rejected and the remaining references are used to re-align the retention times in each acquisition by a probabilistic calibration system.

Figure 1B:
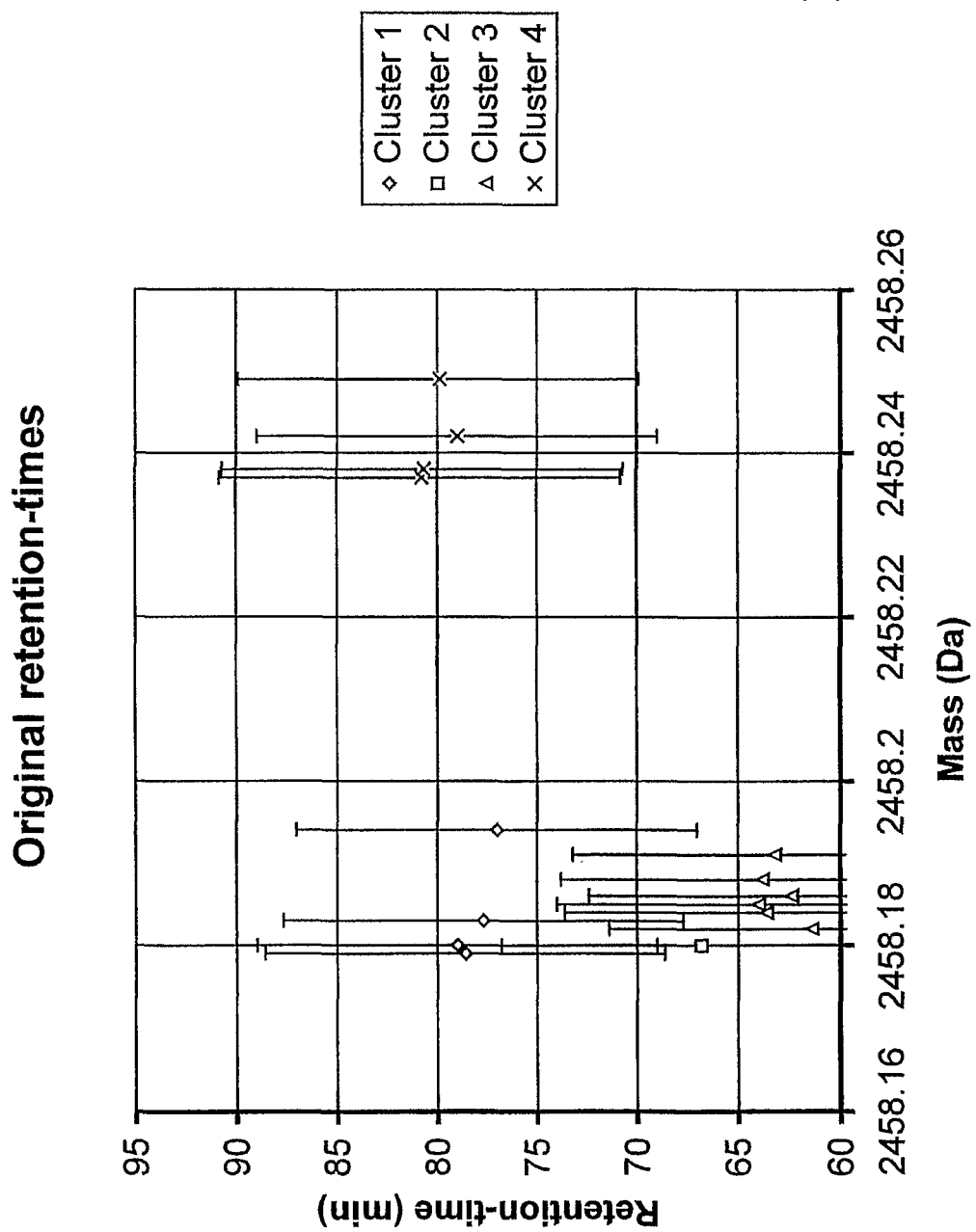
Figure 2A:
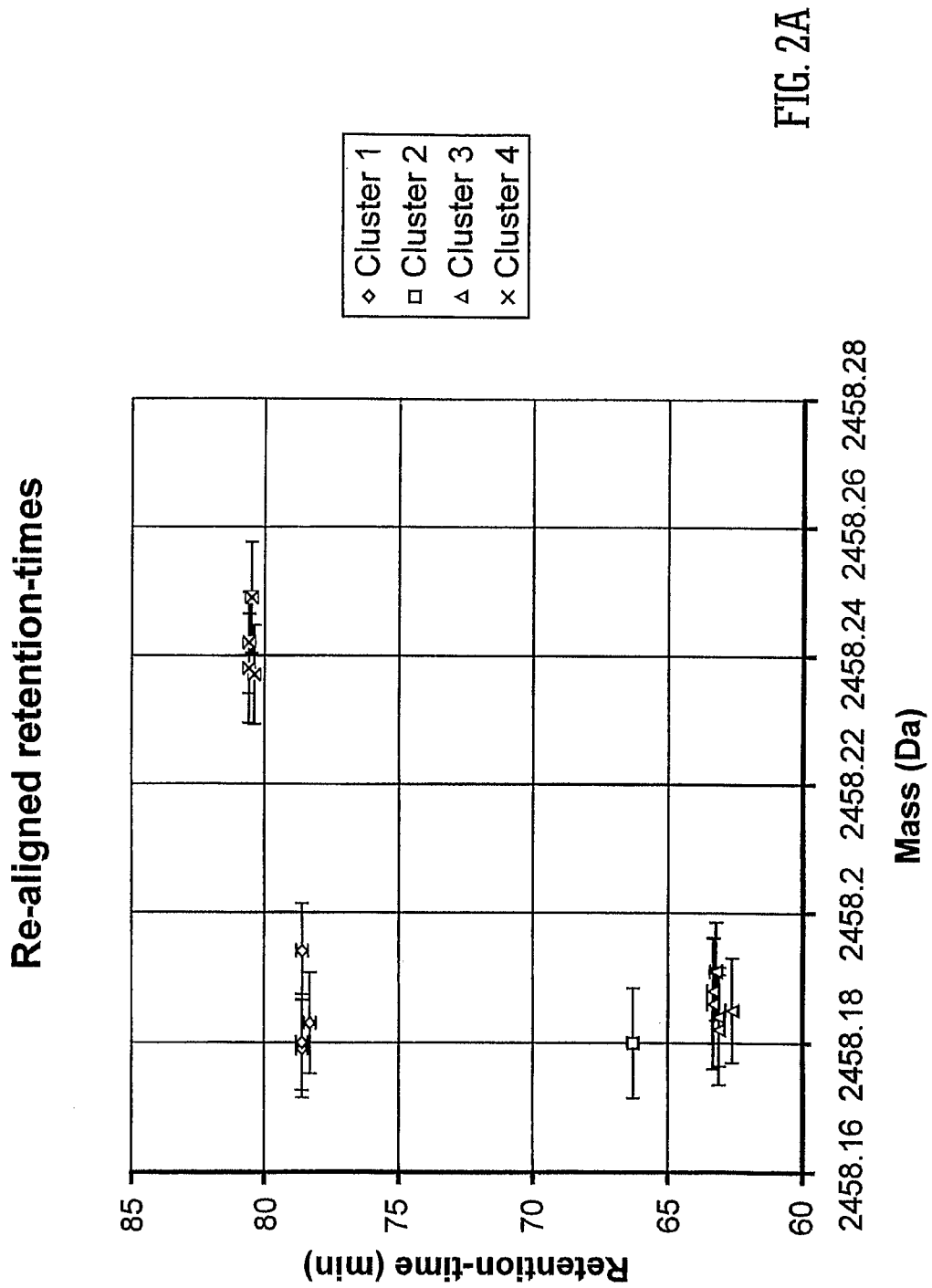
Figure 2B:
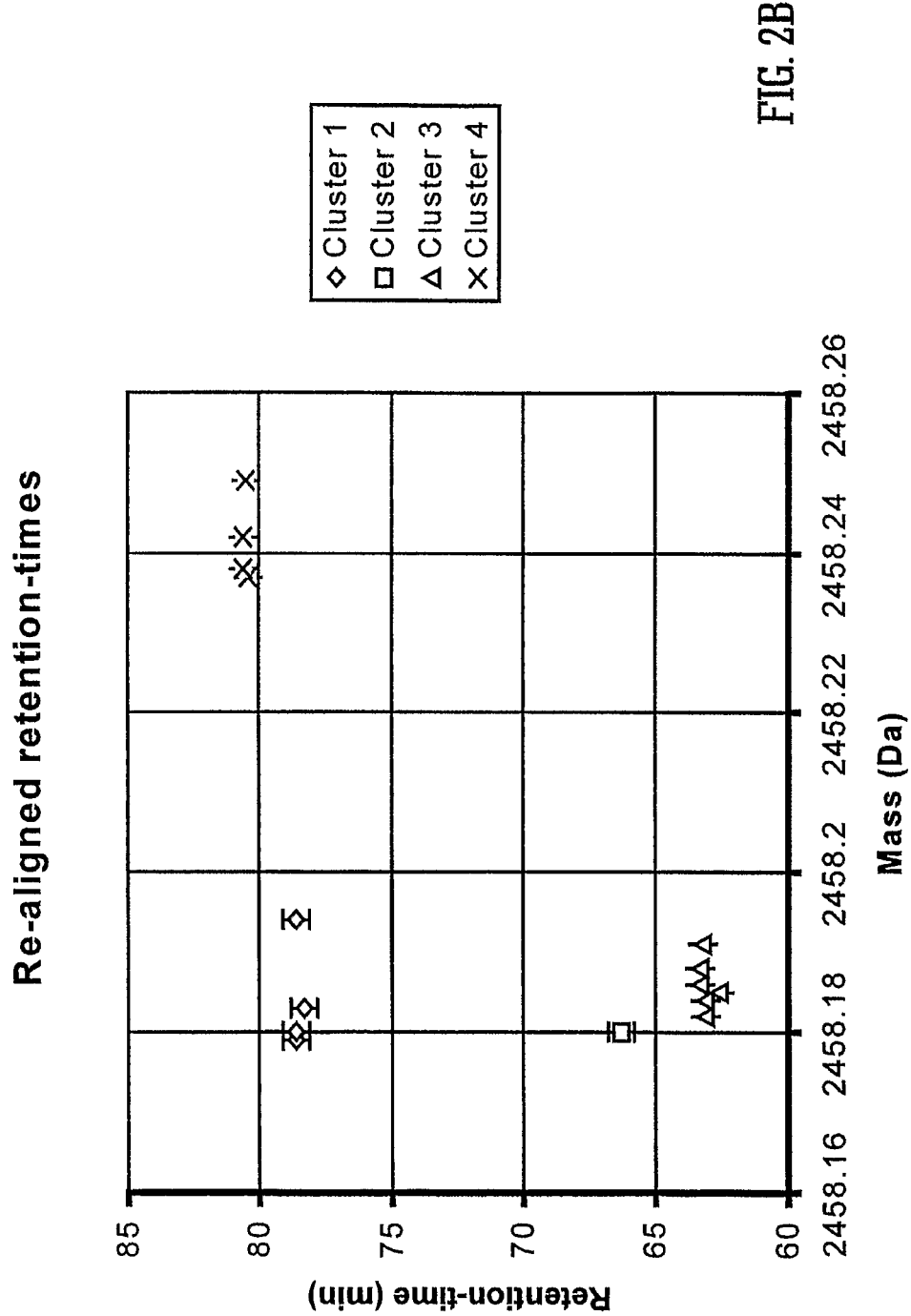

Various embodiments of the present invention will now be described, by way of example only, and with reference to the accompanying drawings in which:

FIG. 1A shows a graph of mass against original retention time and shows error bars for the mass measurements and FIG. 1B shows a related graph of mass against original retention time for the same data as shown in FIG. 1A but shows instead error bars for the retention time measurements; and FIG. 2A shows a graph of mass against retention time according to the preferred embodiment wherein the retention times have been realigned and shows the same error bars for the mass measurement as in FIG. 1A, and FIG. 2B shows a related graph of mass against retention time for the same data as shown in FIG. 2A but shows the significantly reduced error bars for the retention time measurements resulting from the preferred embodiment.

A preferred embodiment of the present invention will now be described. The table below relates to fifteen data points observed from liquid chromatography mass spectrometry experiments relating to four separate species of ions all having the same nominal mass of 2458 Daltons but which have different chromatographic retention times.

The masses of each of the peptide ions and their corresponding retention times are shown together with the standard deviation in each mass measurement. The data points were acquired from six separate acquisitions and were initially assigned to four separate clusters i.e. four distinct species of ion were believed to be present in the sample being analysed. The experimental data was then processed in accordance with the preferred embodiment to obtain re-aligned retention times.

| Datum | Acquisition | Mass (Da) | Mass SD | Original RT | Re-aligned RT | RT SD | Cluster |
|---|---|---|---|---|---|---|---|
| 1 | 1 | 2458.179 | 0.0075 | 78.6 | 78.6 | 0.21 | 1 |
| 3 | 6 | 2458.180 | 0.0074 | 79.0 | 78.6 | 0.22 | 1 |
| 5 | 2 | 2458.183 | 0.0078 | 77.7 | 78.3 | 0.22 | 1 |
| 11 | 5 | 2458.194 | 0.0074 | 77.0 | 78.6 | 0.22 | 1 |
| 2 | 3 | 2458.180 | 0.0085 | 66.8 | 66.3 | 0.22 | 2 |
| 4 | 5 | 2458.182 | 0.0085 | 61.4 | 63.1 | 0.22 | 3 |
| 6 | 3 | 2458.184 | 0.0076 | 63.6 | 63.1 | 0.22 | 3 |
| 7 | 4 | 2458.185 | 0.0080 | 64.0 | 62.6 | 0.25 | 3 |
| 8 | 2 | 2458.186 | 0.0100 | 62.4 | 63.3 | 0.22 | 3 |
| 9 | 6 | 2458.188 | 0.0081 | 63.8 | 63.3 | 0.22 | 3 |
| 10 | 1 | 2458.191 | 0.0075 | 63.2 | 63.2 | 0.22 | 3 |
| 12 | 6 | 2458.237 | 0.0077 | 80.8 | 80.4 | 0.22 | 4 |
| 13 | 1 | 2458.238 | 0.0085 | 80.7 | 80.6 | 0.21 | 4 |
| 14 | 5 | 2458.242 | 0.0079 | 79.0 | 80.6 | 0.22 | 4 |
| 15 | 2 | 2458.249 | 0.0086 | 79.9 | 80.5 | 0.22 | 4 |

FIGS. 1A and 1B show plots of the fifteen experimental data points i.e. before the retention times have been re-aligned in accordance with the preferred embodiment. FIG. 1A shows a plot including mass error bars and FIG. 1B shows the same plot including error bars for retention time.

As will be understood by those skilled in the art, if the same sample is repeatedly analysed by liquid chromatography mass spectrometry then whilst the mass or mass to charge ratios of analytes ions may be fairly accurately reproduced from experiment to experiment, there will tend to be larger variations in the measured chromatographic retention time i.e. liquid chromatography is less reliable or reproducible than mass analysis. From one LC run to the next, the overall scale of the LC data will tend to drift and this drift can be particularly problematic when seeking to cluster or recognise the same species of component, molecule or analyte present in two or more separate samples. The drift in chromatographic retention times may be due to temperature or pressure drifts or due to the LC column clogging up.

It will be appreciated that whilst some analytes in separate experiments or samples can be confidently recognised as being the same species without requiring substantial processing of the data, it is often not possible to confidently recognise other species at least initially. The preferred embodiment therefore provides an important tool in being able to handle complex mixtures and effectively enables the chromatographic time scales for two sets of data to be realigned so that a much greater number of components in the two data sets can be confidently recognised as comprising the same species.

The data shown in FIGS. 1A and 1B has been initially clustered using the matrix method approach discussed above. Although the error bars in the retention time for the experimental data are relatively large (as can be seen from FIG. 1B), nonetheless the matrix method approach was able to separate the data into four distinct clusters indicating that to a high level of certainty four different species of peptides or analytes are present.

The error bars shown in FIGS. 1A and 1B are those estimated for the experiments and relate to calibrated, de-isotoped and charge-state reduced masses. The error bars on retention times as shown in FIG. 1B were derived from a user input estimate of retention time precision. The retention time error bars are preferably chosen to represent the worst possible errors, rather than what might be typical, to ensure that the retention times are not treated with greater significance than is justified in the initial clustering procedure.

The experimental data as presented in the table above and as shown in FIGS. 1A and 1B was then processed according to the preferred embodiment with the result that the chromatographic retention times were significantly realigned across the data sets.

FIGS. 2A and 2B show experimental data after processing and clustering according to the preferred embodiment. As is apparent from these figures especially FIG. 2B, the retention times of the data have been significantly realigned such that it is apparent that the four clusters are indeed separate and distinct clusters.

It will appreciated that the data presented in the table above and as shown in FIGS. 1A, 1B, 2A and 2B represents only a very small amount of data. The reduced amount of data is presented simply for reasons of clarity. In practice, the data sets may comprise thousands of data points in which case the significant improvement in clustering of data according to the preferred embodiment becomes even more pronounced.

The data points have been processed according to the preferred embodiment. It is apparent that the preferred method of processing the experimental data has been effective in realigning the retention times of the two data sets thereby enabling like species in the two different samples to be confidently correlated. As can be seen from comparing FIG. 1A and FIG. 2A the mass error bars for each data point remain the same after realigning the retention times according to the preferred embodiment i.e. according to the preferred embodiment the errors in the mass or mass to charge ratio determinations are substantially unaffected by the preferred embodiment.

The retention time error bars in the FIG. 2B are derived automatically from the probabilistic analysis according to the preferred embodiment. The error bars encompass the confidence in the determination for each retention time calculation and the confidence in the re-alignment factor applied to each data point. The confidence in the determination for each retention time calculation is largely determined by how many ions there are in the peak, the more ions the higher the confidence. If the retention time of a peak and the nearest reference peak are very similar then the confidence in the calibration at that retention time is high. If the retention time of the peak falls mid-way between those of two reference peaks then the confidence in the calibration is not so high. If the nearest two reference peaks are a long way apart then the confidence in the calibration at the mid-way point is even less.

According to a less preferred embodiment k-means clustering may initially be used to cluster data rather than using the preferred matrix method which was employed to initially cluster the data (as shown in FIGS. 1A and 1B). If data is initially clustered using k-means clustering then the clustering of data is then preferably further improved upon by applying the preferred probabilistic approach to clustering the data.

Given the nature of the peptide mass sufficiency distribution, it is contemplated that a non-uniform or Gaussian prior distribution of peptide mass may be more appropriate in the calculation of the likelihood $L(x_i,x_j)$.

It is also contemplated that the mass and retention time ordering of data used in the iterative solution improvement stage may be replaced by an alternative approach based on Hilbert space-filling curves. This would improve the preservation of the locality of the two dimensional mass-retention time plane.

Although the present invention has been described with reference to preferred embodiments, it will be understood by those skilled in the art that various changes in form and detail may be made without departing from the scope of the invention as set forth in the accompanying claims.

The invention claimed is:

1. A method of mass spectrometry comprising:
determining a first physico-chemical property and a second physico-chemical property of components, molecules or analytes in a first sample, wherein said first physico-chemical property comprises mass or mass to charge ratio and said second physico-chemical property comprises elution time, hydrophobicity, hydrophilicity, migration time, or chromatographic retention time;
determining a first physico-chemical property and a second physico-chemical property of components, molecules or analytes in a second sample, wherein said first physico-chemical property comprises mass or mass to charge ratio and said second physico-chemical property comprises elution time, hydrophobicity, hydrophilicity, migration time, or chromatographic retention time; and
probabilistically associating, clustering or grouping data relating to components, molecules or analytes in said first sample with data relating to components, molecules or analytes in said second sample, wherein the data is obtained by performing processing of the first sample and the second sample the processing including performing mass spectrometry using a mass spectrometer, and the method further including:
clustering the data into one or more first clusters of data points; and
probabilistically clustering the data points into one or more second clusters of data points.

2. A method as claimed in claim 1, wherein components, molecules or analytes in said first sample and/or said second sample and/or further samples are separated by liquid chromatography.

3. A method as claimed in claim 1, wherein components, molecules or analytes in said first sample and/or said second sample and/or further samples are separated from other components, molecules, or analytes by any of: (i) High Performance Liquid Chromatography ("HPLC"); (ii) anion exchange; (iii) anion exchange chromatography; (iv) cation exchange; (v) cation exchange chromatography; (vi) ion pair reversed-phase chromatography; (vii) chromatography; (viii) single dimensional electrophoresis; (ix) multi-dimensional electrophoresis; (x) size exclusion; (xi) affinity; (xii) reverse phase chromatography; (xiii) Capillary Electrophoresis Chromatography ("CEC"); (xiv) electrophoresis; (xv) ion mobility separation; (xvi) Field Asymmetric Ion Mobility Separation ("FAIMS"); or (xvii) capillary electrophoresis.

4. A method as claimed in claim 1, further comprising forming a single data set from the data relating to said first sample and/or the data relating to said second sample and/or data relating to further samples.

5. A method as claimed in claim 1, further comprising comparing data points related to components, molecules or analytes in said first sample with data points related to components, molecules or analytes in said second sample and/or data points related to components, molecules or analytes in further samples.

6. A method as claimed in claim 5, wherein each data point comprises a value of said first physico-chemical property and/or a value of said second physico-chemical property.

7. A method as claimed in claim 1, wherein said step of clustering said data into one or more first clusters of data points comprises probabilistically clustering said data points.

8. A method as claimed in claim 1, further comprising assessing a closeness of data points on a pairwise basis.

9. A method as claimed in claim 1, further comprising calculating probabilistically a likelihood that two data points relate to the same component, molecule or analyte.

10. A method as claimed in claim 1, further comprising interrogating said one or more second clusters of data points to determine one or more third clusters of data points which include one and only one data point representing a molecule, analyte or ion from said first sample, said second sample and any further samples.

11. A method as claimed in claim 10, wherein the data relating to said second physico-chemical property each of said one or more third clusters of data points is averaged to form an average value for said second physico-chemical property.

12. A method as claimed in claim 11, wherein data of one or more data points clustered to form said one or more third clusters of data points is adjusted such that said average value becomes the value of said second physico-chemical property for said data points.

13. A method as claimed in claim 11, further comprising determining a calibration function to correlate or correct data relating to an observed second physico-chemical property with said average value for said second physico-chemical property.

14. A method as claimed in claim 13, further comprising adjusting data points from each sample or from all samples to align, recalibrate, correct or reassign the second physico-chemical property for all data sets.

15. A method as claimed in claim 1, further comprising comparing adjusted data points related to components, molecules or analytes in said first sample with adjusted data points related to components, molecules or analytes in said second sample and/or adjusted data points related to components, molecules or analytes in further samples.

16. A method as claimed in claim 15, wherein each adjusted data point comprises an unadjusted value of said first physico-chemical property and/or an adjusted value of said second physico-chemical property.

17. A method as claimed in claim 1, further comprising, determining an intensity of first components, molecules or analytes in said first sample and/or first components, molecules or analytes in said second sample and/or first components, molecules or analytes in further samples.

18. A method as claimed in claim 17, further comprising comparing the intensity of said first components, molecules or analytes in said first sample with corresponding first components, molecules or analytes in said second sample and/or further samples, wherein said first components, molecule or analytes belong to the same association, clustering or grouping of data.

19. A method as claimed in claim 1, wherein said components, molecules or analytes in said first sample are substantially the same as said components, molecules or analytes in said second sample and/or further samples.

20. A method as claimed in claim 1, wherein said components, molecules or analytes are endogenous or exogenous to said first sample and/or said second sample and/or further samples.

21. A method as claimed in claim 1, wherein either: (i) said first sample is taken from a diseased organism and said second sample is taken from a non-diseased organism; (ii) said first sample is taken from a treated organism and said second sample is taken from a non-treated organism; or (iii) said first sample is taken from a mutant organism and said second sample is taken from a wild type organism.

22. A method as claimed in claim 1, further comprising identifying one or more of said components, molecules or analytes in said first sample and/or second sample and/or further samples.

23. A method as claimed in claim 1, wherein one or more components, molecules or analytes in said first sample and/or one or more components, molecules or analytes in said second sample and/or one or more components, molecules or analytes in further samples are only identified if an intensity of one or more components, molecules or analytes in said first sample differ from an intensity of one or more components, molecules or analytes in said second sample and/or further samples by more than a predetermined amount.

24. A mass spectrometer comprising:
means for determining a first physico-chemical property and a second physico-chemical property of components, molecules or analytes in a first sample, wherein said first physico-chemical property comprises mass or mass to charge ratio and said second physico-chemical property comprises elution time, hydrophobicity, hydrophilicity, migration time, or chromatographic retention time;
means for determining a first physico-chemical property and a second physico-chemical property of components, molecules or analytes in a second different sample, wherein said first physico-chemical property comprises mass or mass to charge ratio and said second physico-chemical property comprises elution time, hydrophobicity, hydrophilicity, migration time, or chromatographic retention time;
means for probabilistically associating clustering or grouping components, molecules or analytes in said first sample with components, molecules or analytes in said second sample;
means for clustering the data into one or more first clusters of data points; and
means for probabilistically clustering the data points into one or more second clusters of data points.

25. A probabilistic method of clustering data comprising:
measuring retention times and masses of a plurality of ions from samples in different experimental acquisitions for liquid chromatography-mass spectrometry experiments performed using a mass spectrometer;
generating a data set comprising said masses and retention times along with estimates of uncertainties inherent in each measurement;
probabilistically associating data between the different experimental acquisitions using mass and retention time;
calculating average retention times where said probabilistically associating results in one or more clusters having one and only one representative from each experimental acquisition;
using said average retention times as references points to calibrate the retention times for each experimental acquisition; and
associating data using mass and retention time in accordance with a precision of chromatography performed and quality of calibration.

* * * * *